United States Patent [19]

Shimshick

[11] 4,250,331

[45] Feb. 10, 1981

[54] REMOVAL OF ORGANIC ACIDS FROM DILUTE AQUEOUS SOLUTIONS OF SALTS OF ORGANIC ACIDS BY SUPERCRITICAL FLUIDS

[75] Inventor: Edward J. Shimshick, Wilmington, Del.

[73] Assignee: E. I. Du Pont de Nemours and Company, Wilmington, Del.

[21] Appl. No.: 83,147

[22] Filed: Oct. 9, 1979

[51] Int. Cl.$^3$ .................. C07C 51/42; C07C 53/00
[52] U.S. Cl. ................................. 562/485; 562/494; 562/580; 562/593; 562/600; 562/606; 562/608
[58] Field of Search ............... 562/600, 606, 608, 485, 562/486, 494, 580, 593

[56] References Cited

U.S. PATENT DOCUMENTS 3,969,196  7/1976  Zosel ..................................... 203/49
4,061,566  12/1977  Modell ................................... 210/32

FOREIGN PATENT DOCUMENTS 521202  5/1940  United Kingdom .
1057911  2/1967  United Kingdom .

Primary Examiner—Alan Siegel

[57] ABSTRACT

Process for recovering carboxylic acids from dilute aqueous solutions of alkali metal salts of such carboxylic acids by mixing such solutions with from 10 to 1000% of a supercritical solution comprising at least 10 mole % carbon dioxide at a pressure from 80 to 500 atm and preferably 100 to 350 atm and at a temperature of from 35° to 200° C. and preferably from 35° to 100° C. whereby the salt reacts with the carbon dioxide to form the carboxylic acid which dissolves in the supercritical fluid. The aqueous phase is allowed to separate from the supercritical fluid phase. The pressure of the supercritical phase is lowered which lowers the solubility of the carboxylic acid in the supercritical fluid so that an acid phase is formed separate from the supercritical fluid phase whereby recovery of the acid is effected.

8 Claims, 2 Drawing Figures

F I G. 1
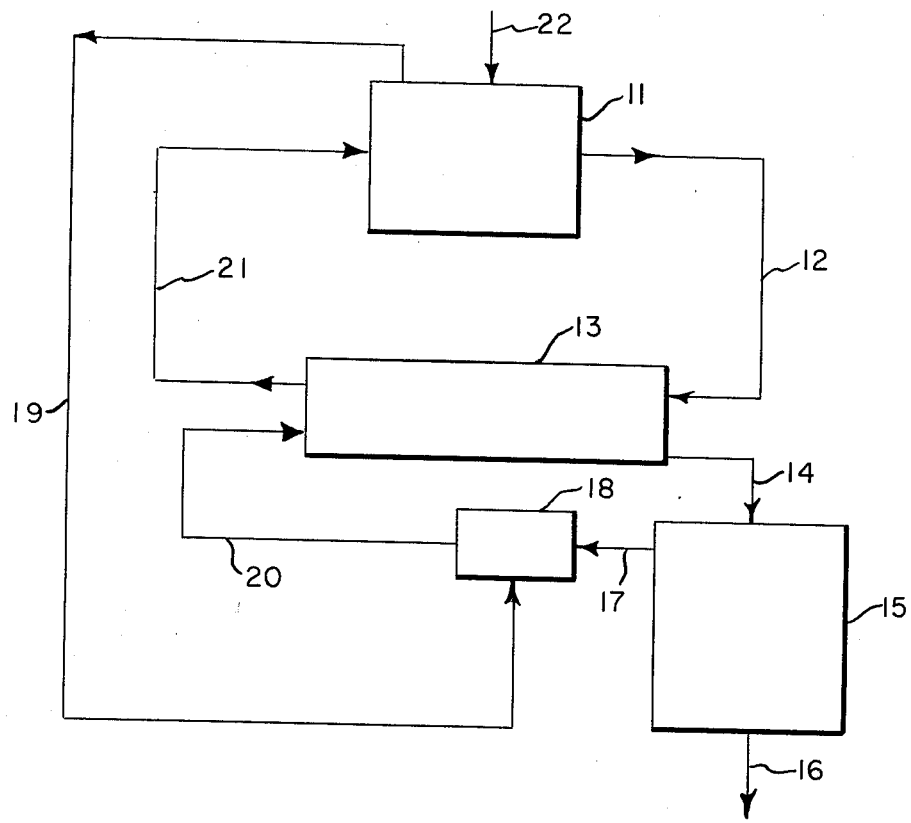
F I G. 2
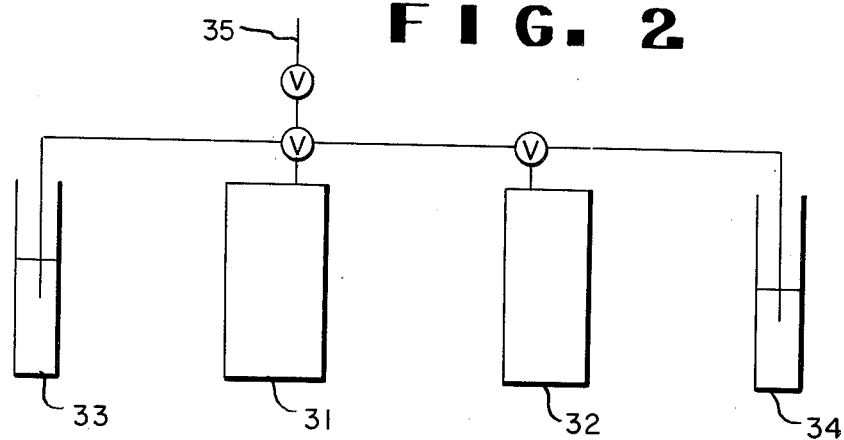

4,250,331

REMOVAL OF ORGANIC ACIDS FROM DILUTE AQUEOUS SOLUTIONS OF SALTS OF ORGANIC ACIDS BY SUPERCRITICAL FLUIDS

BACKGROUND OF THE INVENTION

Field of the Invention

This invention relates to a process for recovering organic carboxylic acids from aqueous solutions of salts of such organic carboxylic acids. The process involves releasing the acid from the salt and extracting the free acid in carbon dioxide at a pressure and temperature high enough for the carbon dioxide to be in the supercritical state.

References

British Pat. No. 1,057,911 discloses extracting organic compounds using various supercritical gases including carbon dioxide and various organic compounds.

U.S. Pat. No. 4,061,566 discloses removing adsorbate from a polymeric adsorbent by contacting the adsorbent with various supercritical fluids including carbon dioxide.

British Pat. No. 521,202 discloses pressuring an alcoholic solution of an alkali metal acetate with carbon dioxide to react the carbon dioxide with the alkali metal acetate to form acetic acid and alkali metal bicarbonate which forms as a precipitate. The acetic acid contained in solution then is mostly in the form of the acid alkali metal acetate. The alcohol is distilled off and the acid alkali metal acetate thermally decomposed to form free acetic acid.

U.S. Pat. No. 3,969,196 discloses separating mixtures containing at least one organic material using a supercritical gas.

SUMMARY

The present invention relates to an extraction process using supercritical carbon dioxide or supercritical carbon dioxide and another supercritical gas to react with a salt of a carboxylic acid in aqueous medium to produce the carboxylic acid which separates from the aqueous phase and dissolves in the supercritical gas phase. The supercritical gas phase is separated from the aqueous phase. The pressure in the supercritical gas phase is then reduced which decreases the solubility of the organic acid in the supercritical gas and causes the formation of an organic acid phase separate from the supercritical gas. The organic acid phase is separated from the supercritical gas phase and the supercritical gas phase is repressured for reuse.

BRIEF DESCRIPTION OF THE DRAWINGS

FIG. 1 is a flow diagram of the process of the present invention used in conjunction with a fermenter.

FIG. 2 is a flow diagram of the apparatus used in the Examples.

DETAILED DESCRIPTION OF THE DRAWINGS

Referring now to FIG. 1, a fermenter 11 produces an organic acid such as acetic acid from an aqueous dispersion of microorganisms growing on a carbohydrate substrate at a pH where an appreciable portion of the acid occurs as the salt. One or more salts of organic acids in aqueous solution are withdrawn from fermenter 11 in line 12 and fed to countercurrent or batch supercritical fluid extractor 13. The supercritical fluid and the organic acid are fed through line 14 to pressure reduction vessel 15 where the supercritical fluid is separated from the organic acid. An energy recovery means, such as a turbine, may be used in the depressurization step. Organic acid is recovered from the system by means of line 16. Supercritical fluid is fed from pressure reduction vessel 15 through line 17 to compressor 18. Make up carbon dioxide is obtained from fermenter 11 and fed to compressor 18 by means of line 19. Additional carbon dioxide can be obtained by stripping the acid in line 16. High pressure supercritical fluid is fed to extractor 13 by means of line 20. The unextracted material from the extractor 13 is fed to fermenter 11 by means of line 21. Make up nutrient is fed to fermenter 11 by means of line 22.

DETAILED DESCRIPTION

The dilute aqueous solution of organic salts suitable for use in the present invention can be obtained from several sources such as fermenter and process streams. Further by controlling conditions, salts of different organic acids can be separated from each other using the process of the present invention.

Suitable salts of organic acids include salts of aliphatic monocarboxylic acids containing from 1 to 20 carbon atoms such as formic acid, acetic acid, butyric acid, caproic acid, lauric acid, and stearic acid. Other suitable salts of organic acids include salts of olefinic monocarboxylic acids containing from 3 to 20 carbon atoms such as acrylic acid, methacrylic acid, ethacrylic acid and oleic acid. Other suitable salts of organic acids include salts of aliphatic dicarboxylic acids containing from 2 to 20 carbon atoms such as oxalic acid, adipic acid and dodecanedioic acid. Other suitable salts include salts of olefinic dicarboxylic acids containing from 4 to 20 carbon atoms such as fumaric acid, maleic acid, itaconic acid and dimethylmuconic acid. Other suitable salts include salts of aromatic carboxylic acids containing from 7 to 20 carbon atoms such as benzoic acid. Other suitable salts include salts of aromatic dicarboxylic acids containing from 8 to 20 carbon atoms such as isophthalic acid and terephthalic acid. Other suitable salts include salts of aliphatic tricarboxylic acids containing 5 to 20 carbon atoms such as citric acid. These acids may contain various substituents such as hydroxyl groups. Such salts include salts of p-hydroxybenzoic acid.

The pressure used in the supercritical carbon dioxide extraction step can vary from 80 to 500 atm with from 100 to 350 atm being the preferred range for carbon dioxide. Above 350 atm and especially above 500 atm the energy needed to compress the supercritical fluid becomes excessive. Below about 100 atm and especially below about 80 atm, the solubility of the carboxylic acids in the supercritical fluid becomes too low and when the pressure is dropped to reduce solubility the critical pressure of carbon dioxide of 73 atm is reached too readily. When using mixtures of supercritical fluids the same upper pressure limits apply but the lower pressure is at least 1.1× the critical pressure of the mixture and preferably 1.3× the critical pressure of the mixture.

Generally the supercritical fluid will be in contact with the dilute carboxylic acid salt solution for from 0.1 to 100 minutes. This time is not particularly critical. After separation of the supercritical fluid and extracted carboxylic acid from the dilute aqueous carboxylic salt solution, the pressure is dropped to reduce the solubility of the carboxylic acid in the supercritical fluid. Generally this drop in pressure will be in the range of from 5 to 85% with from 10 to 60% being the preferred range as determined by the equation $$\left(1 - \frac{P\text{ final}}{P\text{ initial}}\right) \times 100$$

Generally the pressure should not be dropped any more than necessary for economic reasons.

The temperature used in the extraction can vary from just above 31° C., the critical temperature ($T_c$) for carbon dioxide or from just above the critical temperature of whatever mixture of critical fluids are being used up to about 200° C. The preferred temperature range is from 35° C. to 100° C. Above about 100° C. damage to fermentation media may occur. Temperatures above about 200° C. generally are uneconomical. Below about 35° C. it becomes difficult to ensure that the carbon dioxide will remain a supercritical fluid. When exracting fermentation products containing sugar the upper temperature generally will be well below 100° C.

When extracting acids, such as acetic acid, which do not have a particularly high solubility in supercritical carbon dioxide it is desirable to add one or more supercritical gases having a $T_c$ of less than 200° C. and preferably less than 130° C. Preferably at least one of the additional component or components are more polar than carbon dioxide. Thus preferred additional components are more hydrophilic than carbon dioxide and generally will have a net dipole moment. Additional components should form a homogeneous supercritical fluid with carbon dioxide and be stable and unreactive under the extraction conditions. Preferred additional components include, but are not limited to, dimethyl ether, monofluoromethane, monofluoroethane, 1,1,1-trifluoroethane, and trifluoromethane. Less preferred additional components include trifluoromethyl bromide, trifluoromethyl chloride, 1-chloro-2,2,3,3,3-pentafluoroethane, dichlorodifluoromethane, and difluoromethane.

Up to 90 mole % as based on carbon dioxide of the supercritical fluid can be an additional component. Generally, when used, additional components will be present in an amount of from 10 to 60 mole % of the carbon dioxide.

The supercritical fluid generally will be used in an amount of from 10 to 1000 wt % of the dilute acid salt solution being reacted and extracted with from 50 to 200 wt % being the preferred range.

Generally the concentration of the acid salt in the aqueous salt solution being extracted will be from 0.1 to 5 molar. Prior to pressurization the pH of the salt solution will be above the pKa of the organic acid forming the salt so that the majority of the acid is present in salt form. Thus the carbon dioxide (as aqueous carbonic acid) serves as a proton donor and is a reactant. Further, the carbon dioxide simultaneously serves as an extraction fluid.

When using the process of the present invention in conjunction with a fermenter the recycled bicarbonate can serve as a buffer for the fermenter.

Generally the alkali metals such as sodium and potassium and alkaline earth metals such as calcium and magnesium are preferred for forming the salt.

EXAMPLES

The Examples were performed using the apparatus schematically shown in FIG. 2. In all of the Examples except Example 3 high pressure shaker bombs 31 and 32 had an internal volume of about 75 ml. Traps 33 and 34 were graduated cylinders containing 25 ml of water. The supercritical fluid is added to the system by means of line 35. In each Example (except Example 3) 15 ml of aqueous salt solution was added to bomb 31. The bomb was pressurized to the pressure reported in the Examples with supercritical fluid and heated to the temperature reported in the Examples on a shaker. Bomb 32 was connected to bomb 31 and was also heated to the same temperature as bomb 31. Both bombs were shaken for 20 minutes. The phases were allowed to separate for an additional 20 minutes. The valve between bomb 31 and bomb 32 was opened to allow the supercritical fluid to transfer to bomb 32. Except for Example 3 the density of the supercritical fluid drops to an estimated 0.55 times the original density. In Example 10 the final pressure was measured and found to be about one-half the original pressure. Bombs 31 and 32 were removed from the shaker and very slowly vented through water traps 33 and 34 respectively. Bomb 32 was rinsed with 15 ml of water. Assays for acid/acid salt in bomb 31, bomb 32, trap 33 and trap 34 were done by gas chromatography or high performance liquid chromatography. The salt solutions were acidified prior to being assayed. Sodium ion analyses were done in order to correct for any venting of the aqueous solution into bomb 32.

EXAMPLE 1

Carbon dioxide at 2300±200 psig (157.5±13.6 Atm, 15856×10³±1379×10³ Pag) and 53°±2° C. was used to extract butyric acid from 15 ml of aqueous 0.5 molar sodium butyrate solution. The concentration of the butyrate in the aqueous solution dropped by about 17%. About 13% of the total original butyrate was recovered as butyric acid in bomb 32 and traps 33 and 34. The pH of the sodium butyrate solution decreased from 10.2 to 8.0.

EXAMPLE 2

Carbon dioxide at 6200±200 psig (423±13.6 Atm, 42747×10³±1379×10³ Pag) at 77°±2° C. was used to extract butyric acid from 15 ml of aqueous 0.5 M sodium butyrate. The concentration of butyrate in the aqueous phase dropped by about 19%. About 21% of the total butyrate was recovered as butyric acid in bomb 32, trap 33 and trap 34. The pH of the sodium butyrate solution dropped from 10.1 to 9.2.

EXAMPLE 3

Carbon dioxide at 2300±200 psig (157.5±13.6 Atm, 15856×10³±1379×10³ Pag) and 52°±2° C. were used to extract butyric acid from 80 ml of aqueous 0.5 M sodium butyrate (bomb 31 was a 400 ml bomb, bomb 32 was a 75 ml bomb). About 4% of the butyrate was recovered as butyric acid in bomb 32 and trap 34. The final density of the carbon dioxide was estimated to be about 0.8 that of the original density.

EXAMPLE 4

Carbon dioxide 90 mole %/dimethyl ether 10 mole % at 2000±200 psig (137±13.6 Atm, 13790×10³±1379×10³ Pag) and 52°±2° C. was used to extract butyric acid from 15 ml of aqueous 0.5 M sodium butyrate. The concentration of the butyrate in the aqueous phase dropped by about 26%. About 23% of the total butyrate was recovered as butyric acid in bomb 32, trap 33 and trap 34. The pH of the aqueous phase dropped from 10.1 to 8.8.

EXAMPLE 5

Monochlorotrifluoromethane 10 mole %/carbon dioxide 90 mole % at 2100±200 psig (143±13.6 Atm, 14479×10³±1379×10³ Pag) and 52°±2° C. was used to extract butyric acid from 15 ml of aqueous 0.5 M sodium butyrate. The butyrate concentration in the aqueous phase dropped by about 13%. About 11% of the total butyrate was recovered as butyric acid in bomb 32, trap 33 and trap 34. The pH in the aqueous phase dropped from 10.1 to 8.5.

EXAMPLE 6

Carbon dioxide at 2400±200 psig (164±13.6 Atm, 16547×10³±1379×10³ Pag) and 50°±2° C. was used to extract acetic acid from an aqueous Clostridium thermoaceticum fermentation broth containing about 0.23 M sodium acetate and 0.03 M acetic acid, pH 5.7. About 1% of the acetic acid/sodium acetate in the fermentation broth was recovered as acetic acid in bomb 32, trap 33 and trap 34.

EXAMPLE 7

Dimethyl ether 10 mole %/carbon dioxide 90 mole % at 2400±200 psig (164±13.6 Atm, 16547×10³±1379×10³ Pag) and 50°±2° C. was used to extract acetic acid from 15 ml of the fermentation broth used in Example 6. About 3% of the acetic acid/sodium acetate was recovered as acetic acid in bomb 32, trap 33 and trap 34. The pH of the aqueous phase rose from 5.7 to 5.8.

EXAMPLE 8

Carbon dioxide at 2300±200 psig (157.5±13.6 Atm, 15856×10³±1379×10³ Pag) and 47°±2° C. was used to extract acrylic acid from 15 ml of aqueous 0.25 M sodium acrylate. About 3% of the total acrylate was recovered as acrylic acid in bomb 32, trap 33 and trap 34. The pH of the aqueous phase rose from 5.6 to 6.0.

EXAMPLE 9

Carbon dioxide at 2400±200 psig (164±13.6 Atm, 16547×10³±1379×10³ Pag) and 48°±2° C. was used to extract methacrylic acid from 15 ml of aqueous 0.25 M sodium methacrylate. The sodium methacrylate concentration in the aqueous phase dropped by about 17%. About 10% of the total sodium methacrylate was recovered as methacrylic acid in bomb 32, trap 33 and trap 34. The pH of the aqueous phase rose from 5.8 to 8.6.

EXAMPLE 10

Carbon dioxide at 2600±200 psig (178±13.6 Atm, 17926×10³±1379×10³ Pag) and 50°±2° C. was used to extract benzoic acid and terephthalic acid from 15 ml of an aqueous solution of 0.10 M sodium benzoate and 0.10 M sodium terephthalate, pH 5.8. The sodium benzoate and sodium terephthalate concentrations in the aqueous phase dropped by 8±4% and 12±3%. About 2.5±0.5% of the sodium benzoate and 3±1% of the sodium terephthalate were recovered as benzoic acid and terephthalic acid respectively in bomb 32, trap 33 and trap 34. The pH of the aqueous phase rose from 5.8 to 7.6±0.2 respectively.

EXAMPLE 11

Carbon dioxide at 2400±200 psig (164±13.6 Atm, 16547×10³±1379×10³ Pag) and 48°±2° C. was used to extract butyric acid and hexanoic acid from 15 ml of an aqueous solution of 0.125 M sodium butyrate and 0.123 M sodium hexanoate, pH 9.6. The concentrations of sodium butyrate and sodium hexanoate in the aqueous phase were reduced by about 19% and 53% respectively. About 12% of the sodium butyrate and 24% of the sodium hexanoate were recovered as butyric acid and hexanoic acid respectively in bomb 32, trap 33 and trap 34.

EXAMPLE 12

Carbon dioxide at 2400±200 psig (164±13.6 Atm, 16547×10³±1379×10³ Pag) and 49°±2° C. was used to extract acetic acid from 4 g of an ion exchange resin, Amberlite IRA-68, a gel type, weakly basic anion exchange resin possessing tertiary amine functionality in a crosslinked acrylic matrix, in the acetate form containing 1.15 meq of acetate per g of resin. About 2% of the acetate was recovered as acetic acid.

I claim:

1. A process comprising contacting an aqueous solution of at least one metal salt of a carboxylic acid with a supercritical fluid comprising at least 10 mole % carbon dioxide at from 35° to 200° C. and from 80 to 500 atm, whereby the carbon dioxide reacts with the metal salt of a carboxylic acid to release the free carboxylic acid, forming an aqueous phase and a separate supercritical fluid phase and recovering one or more carboxylic acids derived from a salt or salts of a carboxylic acid contained in the original dilute aqueous solution from the supercritical phase by lowering the pressure of the supercritical fluid from 5 to 85%.

2. The process of claim 1 wherein the pressure used in the contacting step is from 100 to 350 atm.

3. The process of claim 2 wherein the temperature used in the contacting step is from 35° to 100° C.

4. The process of claim 3 wherein the amount of supercritical fluid in the contacting step is from 10 to 1000 wt % of the amount of salt solution.

5. The process of claim 1 wherein the supercritical fluid contains from 10 to 90 mole percent of material which has a dipole moment and has a $T_c$ of less than 200° C.

6. The process of claim 5 wherein the pressure used in the contacting step is from 100 to 350 atm.

7. The process of claim 6 wherein the temperature used in the contacting step is from 35° to 100° C.

8. The process of claim 7 wherein the amount of supercritical fluid in the mixing step is from 50 to 200 mole % of the amount of dilute salt solution.

* * * * *